United States Patent [19]

Smith et al.

[11] Patent Number: 5,006,104

[45] Date of Patent: Apr. 9, 1991

[54] HEART PUMP HAVING CONTRACTIBLE GUIDE MECHANISM FOR PUSHER PLATE

[75] Inventors: William A. Smith, Lyndhurst; Ji-Feng Chen, Cleveland, both of Ohio

[73] Assignee: The Cleveland Clinic Foundation, Cleveland, Ohio

[21] Appl. No.: 268,020

[22] Filed: Nov. 7, 1988

[51] Int. Cl.[5] ........................ A61M 1/12; F04B 43/02

[52] U.S. Cl. .................................... 600/016; 417/395; 623/003

[58] Field of Search .................... 600/16, 17; 417/395, 417/413; 623/3

[56] References Cited

U.S. PATENT DOCUMENTS

| | | | |
|---|---|---|---|
| 0,019,390 | 9/1901 | Rayner et al. | 417/395 |
| 3,263,618 | 8/1966 | Carpenter | 417/395 |
| 3,408,889 | 11/1968 | Golden | 91/169 |
| 3,518,033 | 6/1970 | Anderson | 600/16 |
| 4,334,180 | 6/1982 | Bramm et al. | 600/17 |
| 4,334,838 | 6/1982 | Fessler et al. | 417/395 |
| 4,518,317 | 5/1985 | Inoue | 417/413 |
| 4,525,999 | 7/1985 | Inman | 91/169 |
| 4,779,614 | 10/1988 | Moise | 600/16 |
| 4,854,832 | 8/1989 | Gardner et al. | 417/395 |

FOREIGN PATENT DOCUMENTS

| | | | |
|---|---|---|---|
| 0239723 | 10/1986 | German Democratic Rep. | 600/16 |

*Primary Examiner*—Lee S. Cohen
*Assistant Examiner*—Kennedy J. Schoetzle
*Attorney, Agent, or Firm*—Fay, Sharpe, Beall, Fagan, Minnich & McKee

[57] ABSTRACT

A blood pump is disclosed that is useful as ventricle assist or replacement device comprising a housing having a blood chamber and inlet and outlet ports for the ingress and egress of blood to and from the chamber. A deflectable diaphragm comprises a wall of the blood chamber which upon deflection collapses the blood chamber to urge blood from the chamber out the outlet port. A pusher plate is disposed in association with the diaphragm. The pusher plate includes a collapsible guide mechanism which guides the plate from a first fill position to a second eject position. The guide mechanism can comprise a telescopic guide or straight-line linkage which is collapsible to a first fill position to occupy a substantially lesser space in the housing than when extended to second eject position. The guide mechanism avoids the necessity of a projection from the housing to accommodate a stroke of a guide mechanism. The guide mechanism can be independent of or combined with the drive means.

30 Claims, 6 Drawing Sheets

FIG. 3

HEART PUMP HAVING CONTRACTIBLE GUIDE MECHANISM FOR PUSHER PLATE

BACKGROUND OF THE INVENTION

This invention pertains to the art of fluid pumping devices and more particularly to devices including a diaphragm actuated pumping motion.

The invention is particularly applicable to blood pumps useful as a ventricle assist or replacement devices and is intended for use as a human heart pump. However, it will be appreciated to those skilled in the art that the invention could be readily adapted for other uses as, for example, where similar pumping devices are employed in an environment where highly reliable pumping action is required in a location with a minimal amount of space and which must also avoid interference or action upon items or organs adjacent the pump.

Three overall design objectives motivate this configuration of blood pump. They comprise, first, a better fit in the patient; second, more practical insertion and application for a surgeon; and, finally more controlled pumping action.

Most known blood pumps run on pneumatic systems including an elastomeric diaphragm for pumping the blood that is actuated by an external driver. It has been found that a guide for the diaphragm motion is desirable because absent the guide the diaphragm can move erratically in response to the dynamic actuating and blood pressures and cause problems with an irregular blood pumping motion. Such irregular motions may cause local stagnation, consequent clotting and increased diaphragm stresses and may make it difficult to measure the diaphragm movement and therefore calculate flow volume. The guide will be fixed to the diaphragm with a pusher plate and will provide a smooth linear motion of the diaphragm in response to the actuating pressure. The guide may also limit the maximum travel and prevent damage to blood elements or pump components.

Typically, the pusher plate will be guided by a shaft and bearing arrangement. The shaft is fixed to the pusher plate which is in turn fixed to the diaphragm and the shaft slides through a bearing in a direction perpendicular to the diaphragm. The bearings are fixed in the blood pump housing and the shaft will have a stroke length equal to the actuated movement of the diaphragm.

The particular problem with guide mechanisms of this type is that there is a space requirement within or without the housing equal to the stroke length of the pusher plate shaft. A protrusion in the sidewall of the housing has been employed to accommodate the shaft stroke length when the shaft is in a fill position where the diaphragm is in a disposition to maximize the volume of the blood chamber. When the blood is ejected from the blood chamber and the diaphragm and pusher plate are moved to minimize the volume of the blood chamber, the shaft will be drawn out of the protrusion and into the pump housing.

Although such pump constructions can satisfactorily guide the diaphragm movement, they fail to satisfy all the above cited overall design objectives. The protrusion does not provide a better fit in the patient and insertion of such a cumbersome blood pump in the patient can cause substantial problems for the surgeon. In particular, it has been found that a design having a protrusion in the sidewall will necessitate cutting away some of the rib and adjacent tissue in the patient to accommodate the protrusion when the pump is placed up against the rib cage. When the pump is in the abdomen, the actuator projection places unnecessary and potentially damaging pressure on surrounding organs. Such surgical necessities impose a substantial reluctance against the use of blood pumps of this design.

The present invention contemplates a new and improved pump which overcomes the problems discussed above and others to provide a new pump useful as a ventricle assist or replacement device which provides improved control of pumping action, is simple in design, readily adaptable to a variety of dimensional characteristics, easy to implant, operate and remove, and which provides a better fit in the patient, and practical insertion and application for the surgeon.

BRIEF SUMMARY OF THE INVENTION

In accordance with the present invention, there is provided a blood pump useful as a ventricle assist or replacement device having a movable diaphragm for urging blood from a blood chamber. The diaphragm is guided by a pusher plate including a guide mechanism that obviates a pump housing space requirement equal to the stroke length of the guide mechanism. The guide mechanism contracts or collapses on itself to take up minimum height, volume or space in one dimension while reliably guiding the movement of the pusher plate and diaphragm when the mechanism is extended to a full height second dimension. The pump includes a housing having a blood chamber and a means for blood ingress and egress to and from the chamber. The deflectable diaphragm comprises a wall of the blood chamber. The pusher plate is disposed in association with the diaphragm. The collapsible guide mechanism is disposed in association with the pusher plate for guiding the plate from a first fill position to a second eject position. The mechanism is collapsible to the first fill position to occupy a substantially lesser space in a housing than when extended to the second eject position.

In accordance with another aspect of the present invention, the guide mechanism is collapsible at the first fill position to stroke dimension substantially equal to a housing sidewall depth.

In accordance with a further aspect of the present invention, the guide mechanism means comprises a contractible linkage having a contracted position that avoids an extension from an outer wall of the housing.

In accordance with yet another aspect of the present invention, the guide mechanism comprises a telescopic nesting sleeve assembly in operative engagement with the pusher plate. The assembly is generally disposed in the fluid drive chamber for reciprocal movement in concert with selective operation of the diaphragm.

In accordance with yet another aspect of the invention opposed guide mechanisms are employed interposed between first and second diaphragms to comprise a biventricular replacement device.

In accordance with a more limited aspect of the invention, the guide mechanism itself is actuated by an air drive or motor linkage to drive diaphragm movement.

One benefit obtained by use of the present invention is a pump which is useful as a ventricle assist or replacement device and which includes a guide mechanism for an actuating diaphragm that reliably guides diaphragm motion to avoid erratic movement of the diaphragm during operation.

A further benefit of the present invention is a blood pump that can be actuated with a low pressure fluid drive or a mechanical drive and which takes up a minimum housing volume in one dimension when collapsed to allow the diaphragm to deflect to a fill position in the pump.

Another benefit obtained from the present invention is a blood pump having a housing that avoids outer wall protrusions that accommodated prior known guide mechanisms for a pump configuration that comprises a better fit in the patient and allows better practical insertion and application of the pump for the surgeon.

Other benefits and advantages of the subject new pump will become apparent to those skilled in the art upon a reading and understanding of the specification.

BRIEF DESCRIPTION OF THE DRAWINGS

The invention may take physical form in certain parts and arrangements of parts, the preferred and alternative embodiments of which will be described in detail in this specification and illustrated in the accompanying drawings which form a part hereof and wherein.

DETAILED DESCRIPTION OF THE INVENTION

Figure 1:
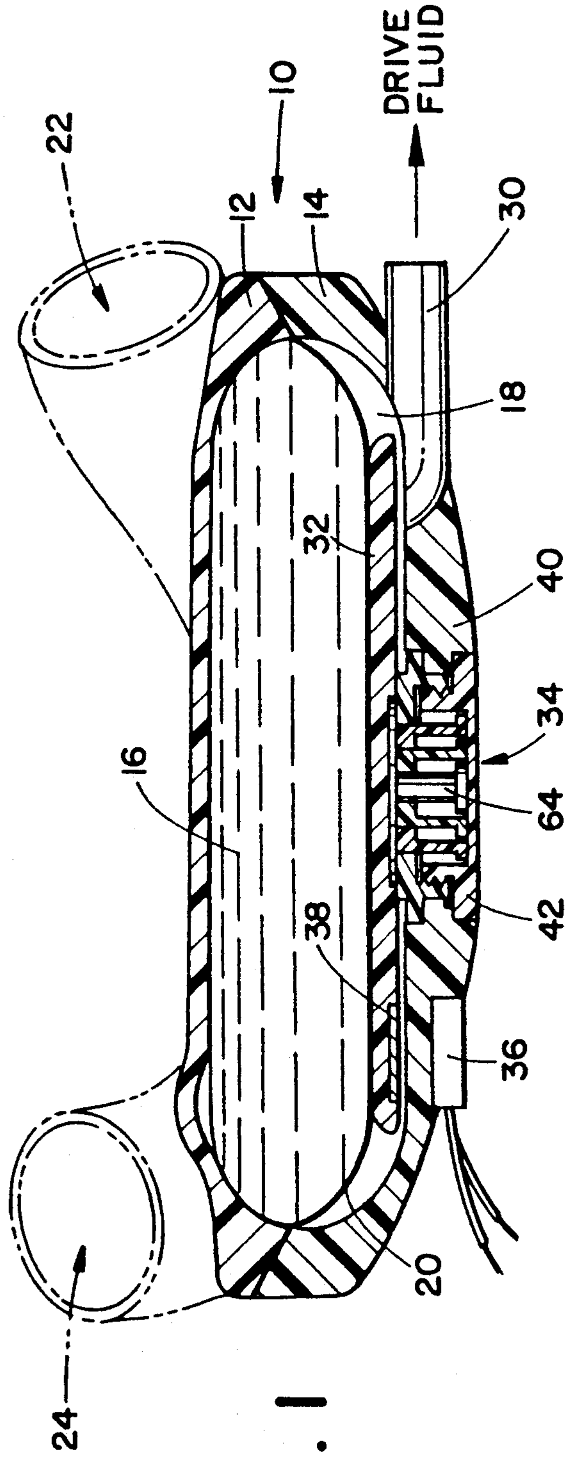
FIG. 1 is a cross-sectional view of a blood pump including a collapsible telescopic guide mechanism wherein the blood chamber is in a first fill position.

Referring now to the drawings wherein the showings are for purposes of illustrating the preferred and alternative embodiments of the invention only and not for purposes of limiting same, the FIGURES show a blood pump 10 useful as a ventricle assist or replacement device comprising an inner housing 12 and an outer housing 14 preferably comprised of epoxy castings or molded polyurethanes and configured in a generally cylindrical configuration. Preferably the pump is a pulsatile, 60 CC per beat displacement device, intended to be driven by a standard intra-aortic balloon pump console (not shown). The housings 12, 14 are sealed together about the periphery (such as by fasteners or glue) to define a blood chamber 16 and a drive chamber 18. The chambers are segregated by a movable elastomeric diaphragm 20 which is typically made of Hexsyn polyolefin rubber although other polymers can also be successfully employed. The blood contacting surfaces are preferably polyurethane coated, but other techniques of obtaining blood compatibility can also be used. A pump inflow or ingress port 22 is blended into the blood compartment tangentially and the outflow or egress port 24 is disposed to pick up and continue the swirl pattern as blood exits the pump. A drive line 30 to the drive chamber 18 provides a low fluid pressure drive to expand the drive chamber 18 and displace the blood on the other side of the diaphragm 20 in the blood chamber 16. Tissue valves (not shown) disposed in the inlet and outflow ports control the flow of blood in the desired flow direction. Typically the outflow goes to the aorta, or pulmonary artery, as appropriate. Venting the drive line 30 to atmosphere permits blood to enter through the inflow port 22 displacing the air in the drive chamber 18 as will hereinafter be more fully explained with regard to the operation of the pump.

It is a feature of the invention that the diaphragm 20 is associated with a pusher plate 32 having a generally circular configuration and joined to the drive chamber wall of the diaphragm for associated movement of the pusher plate with the diaphragm. The pusher plate 32 is associated with a guide mechanism 34 to guide and control the displacement of the diaphragm as it is actuated from a full fill position (FIG. 1) to a full eject position (FIG. 2). The guided pusher plate in association with the diaphragm produces a diaphragm motion that avoids erratic diaphragm movement that may cause problems with locally stagnant blood flow that can cause clotting, prevents uneven diaphragm stress patterns and allows the calculation of a predictable flow volume in relation to diaphragm movement from the fill position to the eject position.

The strokes of the diaphragm may be sensed and counted by a Hall sensor 36 disposed in the outer housing substantially adjacent a magnet 38 mounted in the pusher plate 32.

Figure 2:
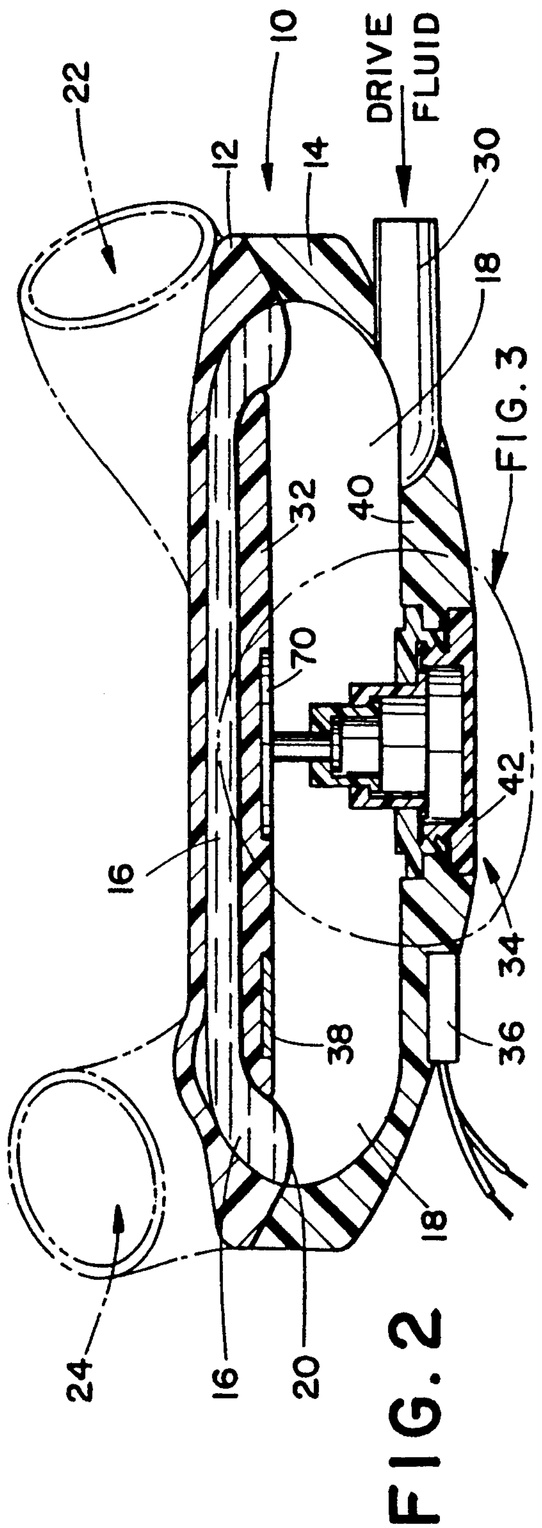
FIG. 2 is a cross-sectional view of the pump of FIG. 1 showing the diaphragm and blood chamber in a second blood eject position.
Figure 3:
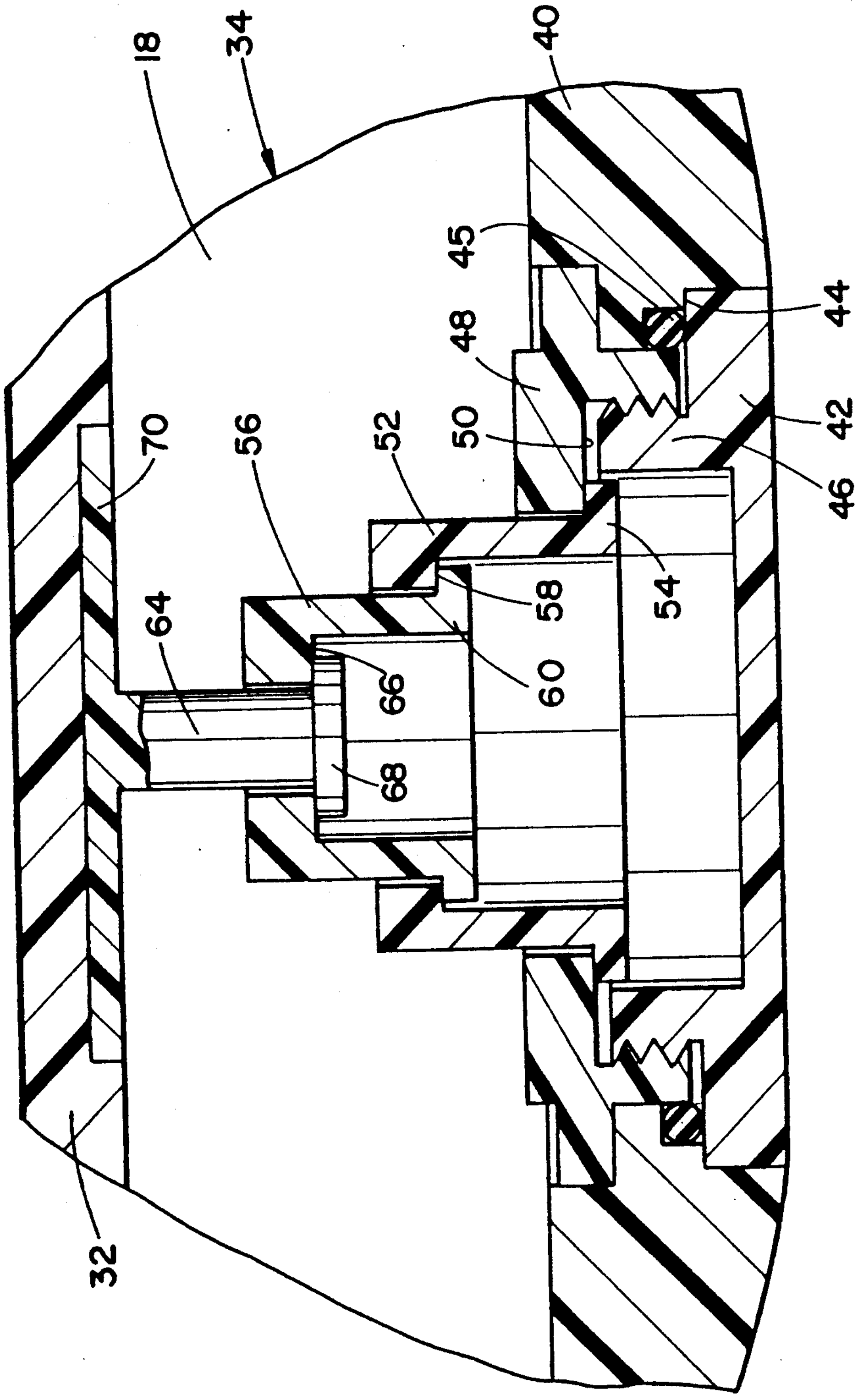
FIG. 3 is an enlarged cross-sectional view of the telescopic guide mechanism in the position illustrated in FIG. 2.

With particular reference to FIGS. 1, 2 and 3 a telescopic guide mechanism 34 is employed to guide the movement of the pusher plate and diaphragm. The guide mechanism is mounted in the outer housing sidewall 40 with a cap 42 that contacts sidewall 40 at inner face surfaces 44, compressing a seal 45. The cap includes a threaded lip portion 46 for threaded reception of the guide mechanism outer sleeve 48. Sleeve 48 includes an inner face 50 sized to retain a middle sleeve 52 at the sleeve flange 54 when the guide mechanism is extended as shown in FIG. 3. Similarly, middle sleeve 52 retains inner sleeve 56 at a middle sleeve inner face 58 in abutment with the inner sleeve flange 60. The inner sleeve 56 retains a pusher plate shaft 64 by the inner sleeve, inner face 66 in abutting engagement with the shaft stop 68. The pusher plate shaft 64 includes a flange 70 fixedly secured to the pusher plate 32.

As can be seen with particular reference to FIGS. 2 and 3 when the blood pump is in a full eject position so that the volume of the blood chamber 16 is minimized, the guide mechanism sleeves 52, 56 and the shaft stop 64 are extended away from the guide mechanism cap 42 in a telescopic extension. However, when the blood pump is in a full fill position so that the blood chamber occupies a maximum volume (FIG. 1) it can be seen that the sleeves are nested one within another to occupy a space generally equivalent to the depth dimension of the cap 42 and outer sleeve 48 assembly. This dimension is preferably substantially equivalent to the sidewall dimension 40 so that as the guide mechanism 34 is collapsed or contracted to a fully collapsed position the guide mechanism occupies a thickness substantially less than the distance of the stroke of the guide mechanism. It is to be noted that the movement of the guide mechanism 34 provides a substantially linear motion of the pusher plate 32 for a smooth and controlled diaphragm deflection. That deflection can occur by a low pressure fluid drive which expands the drive chamber 18, thereby deflecting the diaphragm and compressing the blood chamber 16 and urging the blood in the chamber 16 out of the pump 10.

Figure 9:
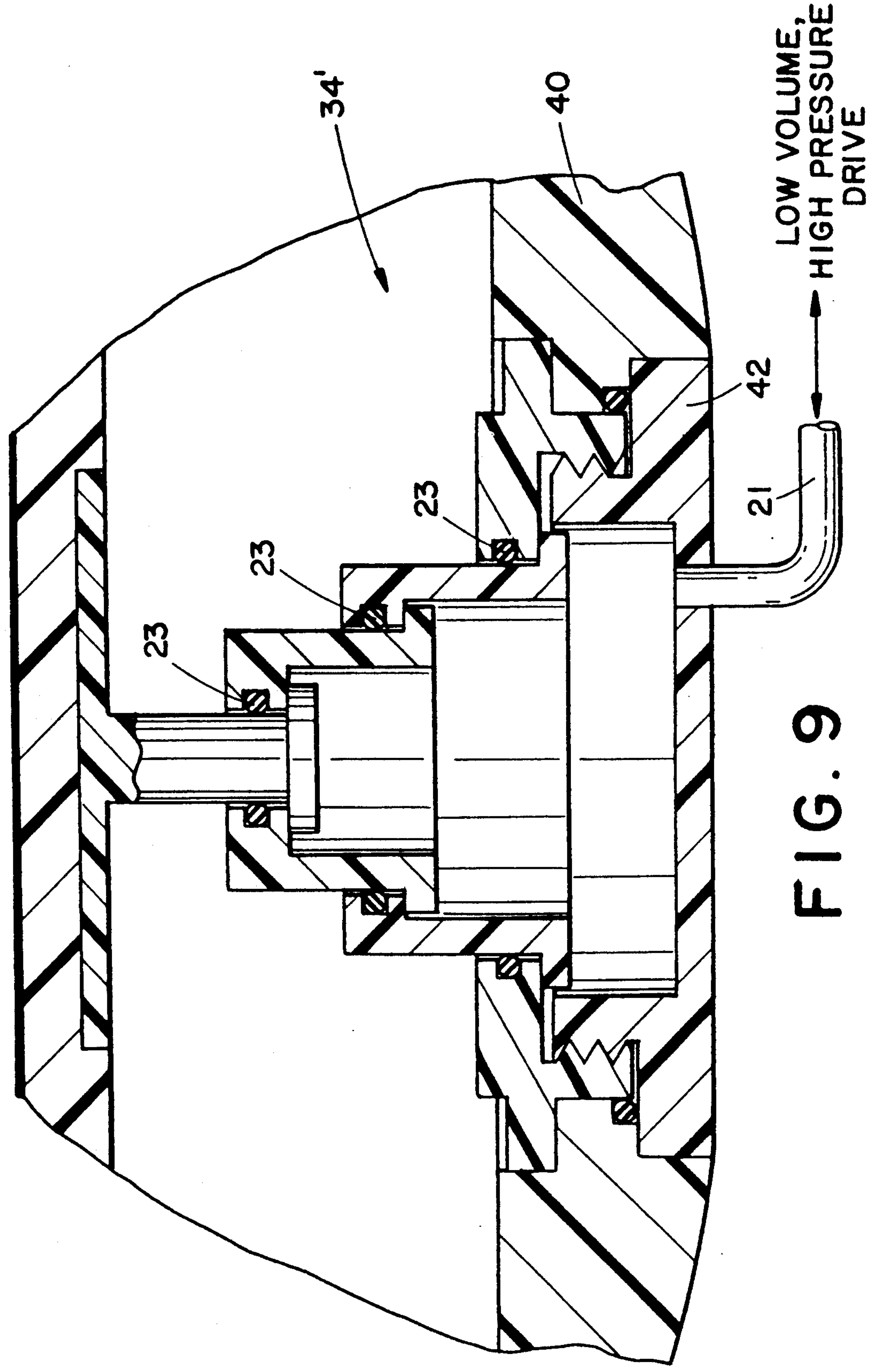

FIG. 9 illustrates an alternative embodiment in which the guide mechanism 34' is also the drive mechanism for the diaphragm 20. A low volume, high pressure drive line 21 expands the guide mechanism 34' during pressurization or vents it for contraction. A plurality of sleeve seals 23 insure the pressurization of the guide mechanism 34' during extension.

Figure 5:
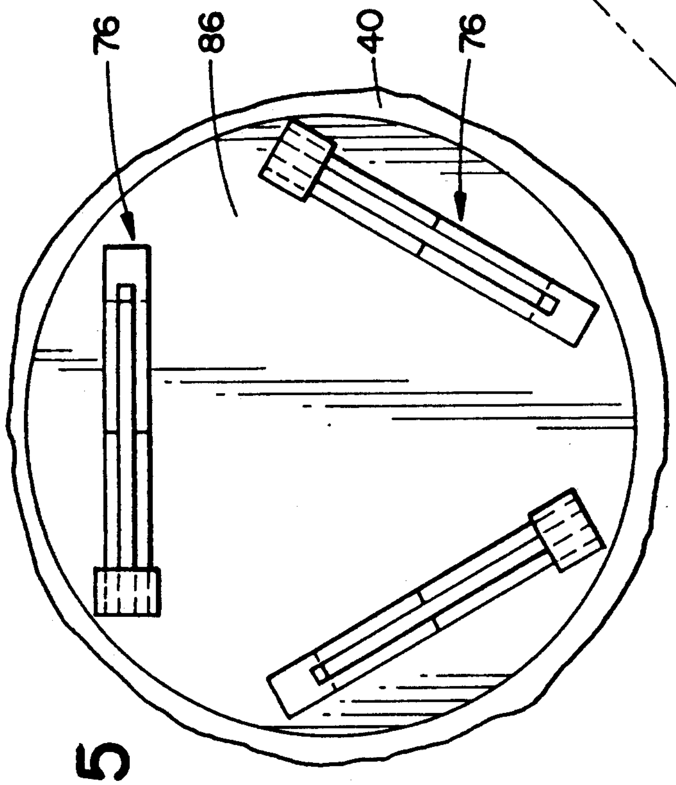
FIG. 5 is a plan view taken along line 5—5 of FIG. 4 illustrating a possible arrangement of linkage guide mechanisms in association with the pusher plate.
Figure 4:
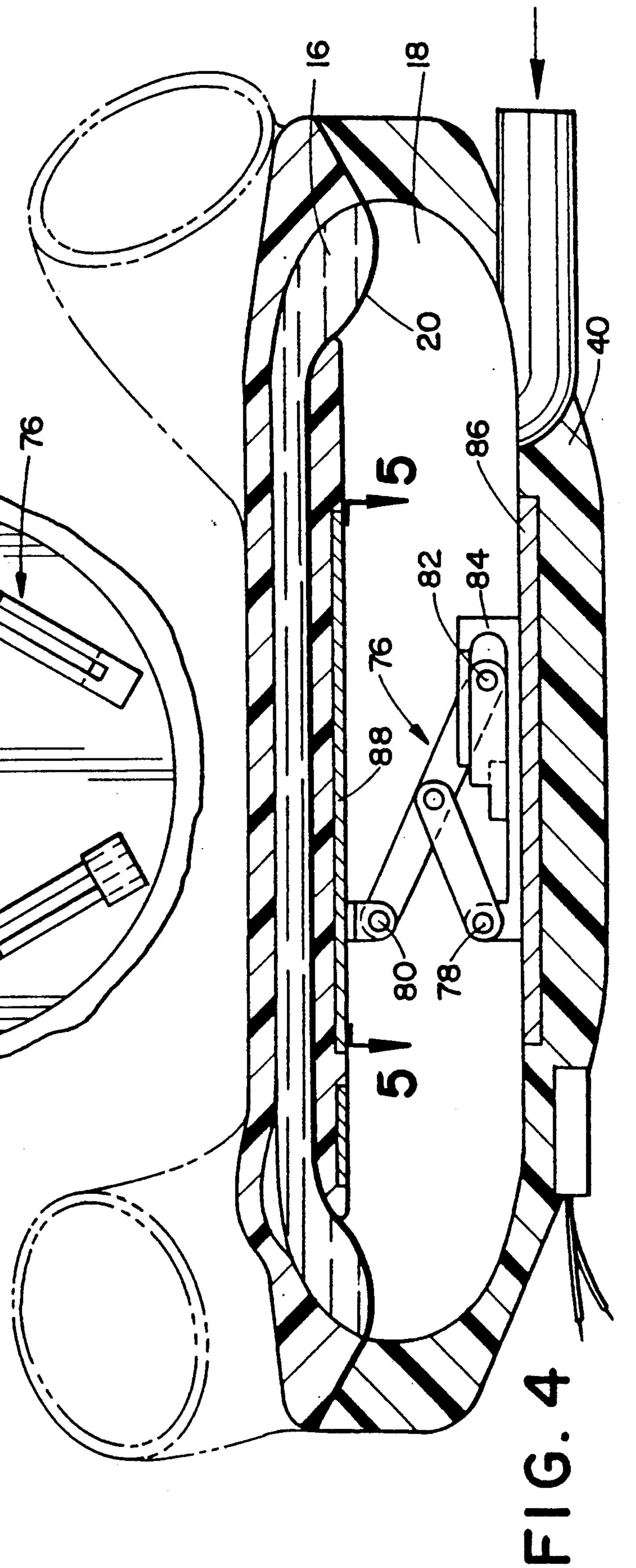
FIG. 4 is a cross-sectional view of an alternative embodiment of the present invention showing a straight-line guide linkage employed as a guide mechanism.

With particular reference to FIGS. 4 and 5, an alternative embodiment of the subject invention is illustrated employing a straight-line motion linkage 76. The linkage 76 provides a Scott Russell straight-line motion between stationary pivot 78 and the pusher plate pivot 80. Sliding pivot 82 is received in a guide 84 so that it may slide along the plane surface defined by the linkage flange 86 secured in the outer housing sidewall 40. The pusher plate pivot 80 is also secured to a pusher plate flange 88 which is similarly secured to the pusher plate 32.

As can be seen with reference to FIG. 5, a plurality of straight-line linkages disposed about the periphery of the pusher plate will provide the desirable guide mechanism for the intended diaphragm actuation. Similar to the telescopic guide mechanism 34, the drive chamber 18 is expanded with the low pressure fluid drive to deflect the diaphragm 20 for urging blood from the blood chamber 16.

FIG. 4 illustrates the straight-line linkage at full eject condition or fully extended between the sidewall 40 and the diaphragm 20. In a fully collapsed or contracted position (not shown) the linkage will have a dimension in the drive chamber 18 substantially equivalent to the depth in the drive chamber of the guide mechanism 84 for the sliding pivot 82. It is also within the scope of the invention to dispose the linkage in a recessed position within the sidewall of the outer housing 40 so that the linkage will not occupy as much space in the drive chamber when contracted as is shown in the embodiment of FIG. 4. With either embodiment though it can be seen that the linkage occupies a substantially lesser amount of space than stroke length due to the collapsible nature of the linkage.

Figure 6:
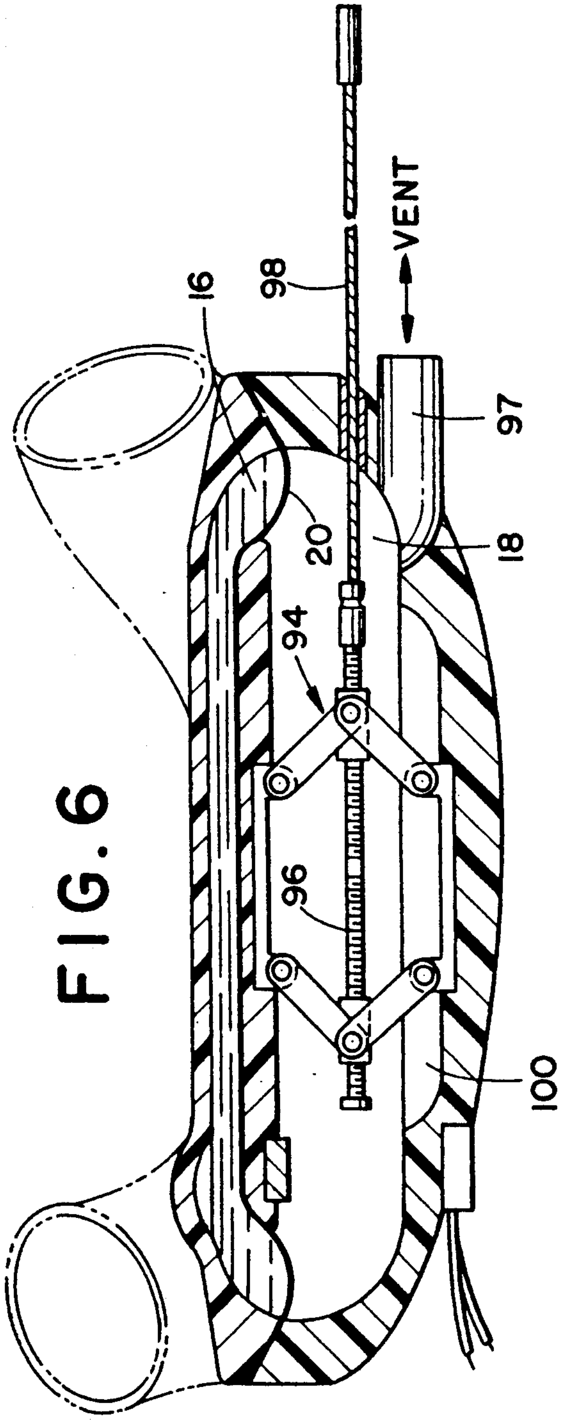
FIG. 6 is another alternative embodiment of the present invention particularly showing a scissors-jack guide mechanism wherein the scissors-jack is operated by a motor drive threaded rod.
Figure 7:
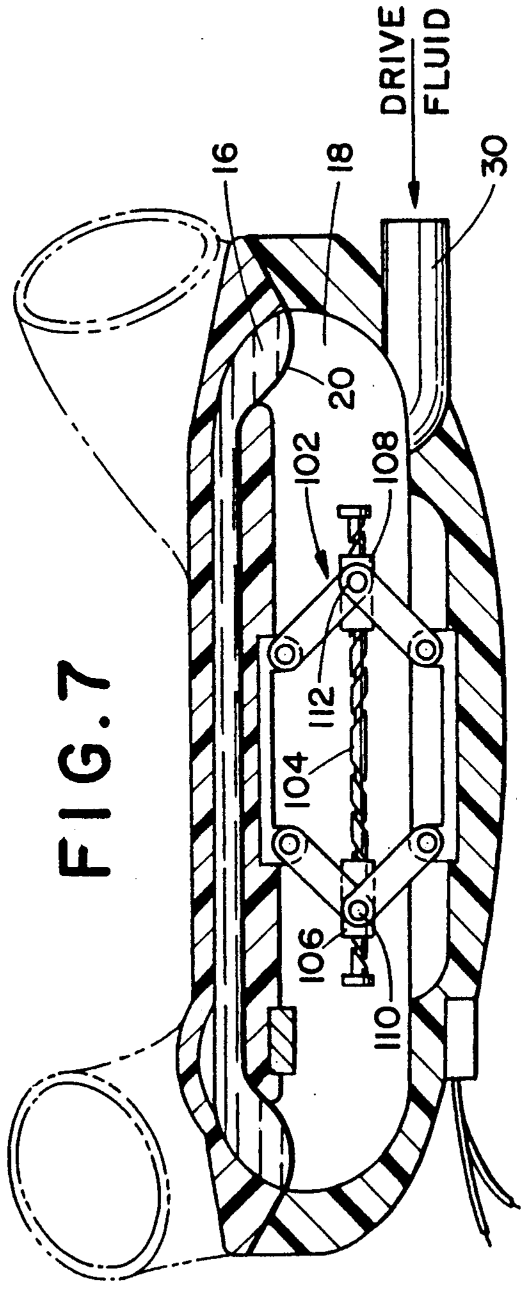
FIG. 7 is yet another alternative embodiment of the subject invention wherein a scissors-jack guide mechanism is employed having a center rod received in bearing cylinders so that the diaphragm may be actuated by a low pressure fluid drive.

With reference to FIGS. 6 and 7, yet another alternative embodiment of the present invention is illustrated wherein a scissors-jack linkage is employed for the straight-line guide mechanism. In this configuration, the guide 94 is also part of the drive mechanism. FIG. 6 illustrates a scissors-jack 94 including a threaded center rod 96 which is motor driven through a flexible cable 98. Selective rotation of cable 98 will extend or contract the jack 94 thereby controlling diaphragm movement. When the linkage 94 is collapsed it is received within a recess 100 of the outer housing sidewall 40. Vent 97 allows the venting of air or fluid from the drive chamber 18. Similar to the other two embodiments of the invention, the scissors-jack will provide a straight-line guide for the pusher plate and diaphragm which will consume a volume in the drive chamber substantially less than the stroke requirement for the guide. There is no need of a protrusion in the housing to accommodate a guide shaft.

With regard to FIG. 7, a similar scissors-jack linkage 102 is employed in which the center rod 104 comprises a shaft received in bearings 106, 108 at center pivots 110, 112, respectively. The embodiment of FIG. 7 is fluid driven with a low pressure fluid drive through drive line 30 to the drive chamber 18.

Figure 8:
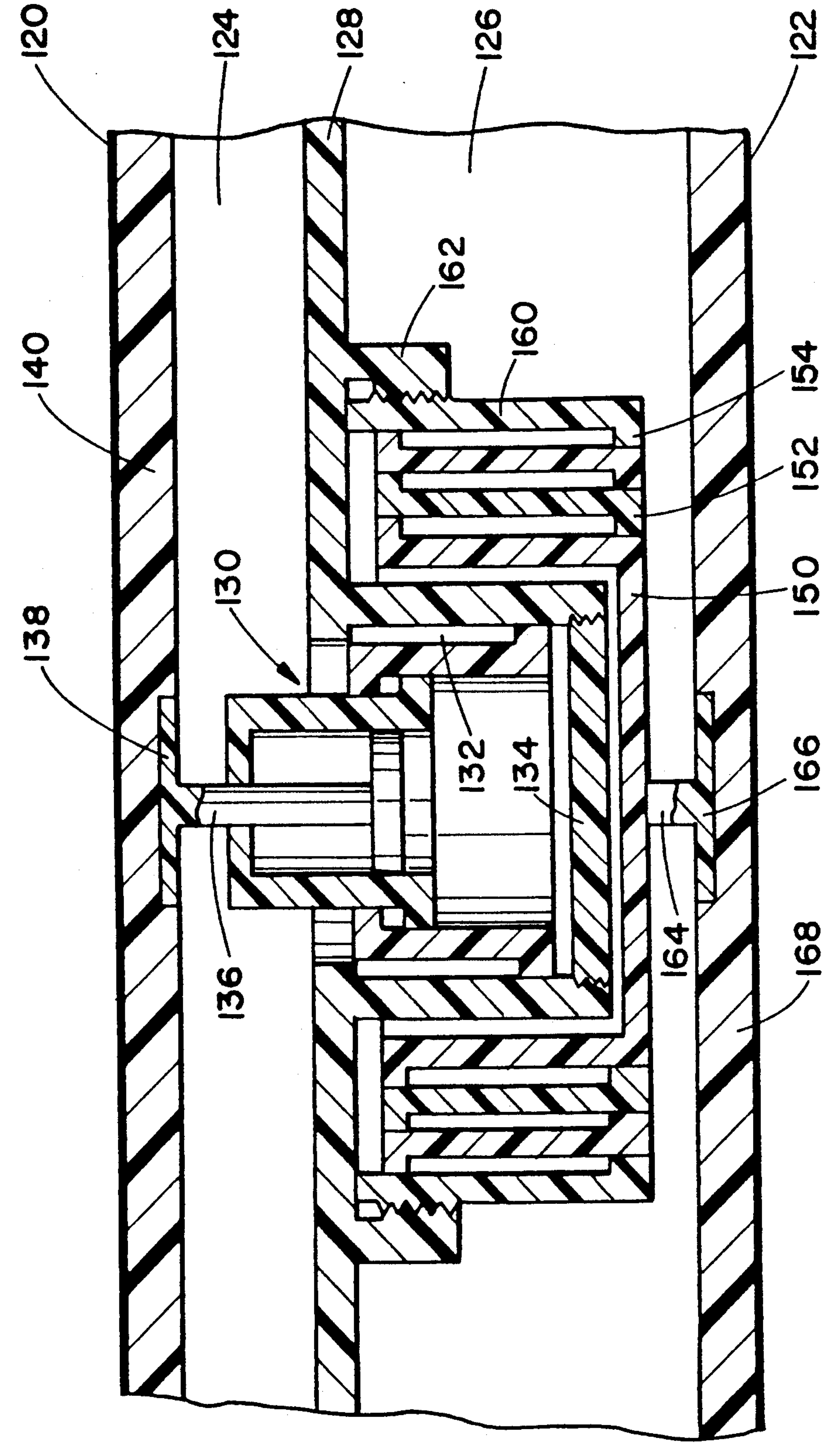
FIG. 8 is cross-sectional view of an alternative embodiment of the invention comprising a double pump ventricle replacement device (Total Artificial Heart) including opposed telescopic guide mechanisms interposed between first and second diaphragms; and, FIG. 9 is an enlarged cross-sectional view of yet another embodiment of the present invention in which the telescopic guide mechanism is pressure driven to direct diaphragm movement.

FIG. 8 illustrates yet another embodiment of the invention particularly suitable for ventricle replacement wherein two pumps are combined in one assembly. First and second opposed diaphragms 120, 122, respectively, are separated by first and second drive chambers 124, 126 and a center wall 128. The center wall 128 separates the drive chambers 124, 126. A first guide mechanism 130 comprising a set of nesting sleeves essentially equivalent to the mechanism shown in FIGS. 1–3 is received in a cavity 132 formed by the center wall 128 and a threaded cap or cover 134. Shaft 136 and flange 138 are associated with first pusher plate 130 for guiding the movement of the first diaphragm 120.

A second larger diameter set of sleeves 150, 152, 154 generally surround the cavity 132 in the center wall 128 and are retained by outer sleeve 160 which is threadedly secured to the center wall at threaded lip portion 162. Second shaft 164 and flange 166 are associated with second pusher plate 168 to control and guide the movement of the second diaphragm 122. Each drive chamber 124, 126 can be independently fluid driven. In this manner a double pump, guided diaphragm device is provided with guide mechanisms having thicknesses not much greater than that of the combined blood cavities.

The invention has been described with reference to the preferred embodiments. Obviously, modifications and alterations will occur to others upon the reading and understanding of the specification. The kinematics literature describes many versions of collapsible mechanisms potentially applicable to blood pump diaphragm guidance. It is our intention to include all such modifications and alterations insofar as they come within the scope of the appended claims or the equivalents thereof.

Having thus described the invention, it is now claimed:

1. A blood pump useful as a ventricle assist or replacement device comprising:

a housing having a blood chamber and a means for blood ingress and egress to and from the chamber;

a deflectable diaphragm that is continuous and has no openings therethrough comprising a wall of the blood chamber;

a pusher plate in operative association with the diaphragm;

means for selectively driving the pusher plate; and, a telescoping guide mechanism in operative association with the pusher plate.

2. The pump as defined in claim 1 wherein the guide mechanism is disposed within the housing.

3. The pump as defined in claim 2 wherein the guide mechanism includes a nestable sleeve in operative engagement with the pusher plate.

4. The pump as defined in claim 1 wherein the housing includes an inner housing and an outer housing, the diaphragm generally disposed intermediate the inner and outer housings to define the blood chamber and a drive chamber.

5. The pump as defined in claim 4 wherein the guide mechanism is generally disposed in the drive chamber and includes means for reciprocally guiding the diaphragm during movement thereof.

6. The pump as defined in claim 5 wherein the guide mechanism includes a base having an outer wall contiguous to an outer wall of the outer housing and generally providing a smooth outer wall for the outer housing to avoid a significant guide mechanism projection from the housing.

7. The pump as defined in claim 1 including means for sensing a travel stroke of the pusher plate.

8. The pump as defined in claim 7 wherein the sensing means comprises a Hall sensor and magnet assembly.

9. A guide mechanism for a blood pump having an elastomeric diaphragm and a pusher plate to support the diaphragm comprising a plurality of nestable sleeves disposed for selective telescopic reciprocatory movement between extended and nested positions, and including means for restricting the pusher plate stroke to a linear motion, and a maximum length.

10. A guide mechanism as defined in claim 9 wherein the plurality of sleeves are sized to occupy a minimum volume when the blood pump is in a full fill position.

11. An implantable ventricular assist or replacement device particularly useful as a blood pump comprising:

a housing having a blood chamber, means for blood ingress and egress to and from the blood chamber, a drive chamber, and a segregating elastomeric diaphragm that is continuous and has no openings therethrough;

means for selectively pressurizing the drive chamber to pump blood to and from the blood chamber;

the diaphragm including a pusher plate bonded thereto and having a plate guide mechanism comprising a plurality of nestable sleeves arranged for telescopic reciprocatory movement between extended and nested positions, said plurality of sleeves having means for limiting preselected maximum travel stroke to restrict enlargement of the drive chamber.

12. The blood pump as claimed in claim 11 wherein the plurality of sleeves is disposed in the drive chamber in both the extended and nested positions to avoid a projection from the housing.

13. The blood pump as claimed in claim 12 further including means for sensing a travel stroke of the pusher plate.

14. A blood pump useful as a ventricle assist or replacement device comprising:

a housing having a blood chamber and a means for blood ingress and egress to and from the chamber;

a deflectable diaphragm comprising a wall of the blood chamber;

a pusher plate in association with the diaphragm;

means for selectively driving the pusher plate; and, a collapsible guide mechanism means in association with the pusher plate for guiding the plate from a first fill position to a second eject position, said mechanism means being collapsible to the first fill position to occupy a substantially lesser space in the housing than when extended to the second eject position.

15. The blood pump as defined in claim 14 wherein the guide mechanism is collapsible at the first fill position to a stroke dimension substantially equal to a housing sidewall depth.

16. The blood pump as defined in claim 14 wherein the guide mechanism means comprises a contractible linkage means for avoiding an extension from an outer wall of the housing.

17. The blood pump as defined in claim 14 further including means for selectively extending the guide mechanism comprising a drive means in operative association with the guide mechanism whereby pressurization of the mechanism extends the mechanism and diaphragm to the eject position.

18. An implantable blood pump comprising:

a housing having a blood chamber and a means for blood ingress and egress to and from the chamber;

a deflectable diaphragm that is continuous and has no openings therethrough comprising a wall of the blood chamber;

a pusher plate in association with the diaphragm;

means for selectively driving the pusher plate; and, a collapsible guide mechanism means in association with the pusher plate for guiding the plate from a first fill position to a second eject position, said mechanism means being collapsible to the first fill position to occupy a substantially lesser space in the housing than when extended to the second eject position.

19. An implantable blood pump as defined in claim 18 wherein the guide mechanism means is collapsible at the first fill position to a stroke dimension substantially equal to a housing sidewall depth.

20. The blood pump as defined in claim 18 further including means for selectively extending the guide mechanism comprising a drive means in operative association with the guide mechanism.

21. An implantable blood pump as defined in claim 17 wherein the guide mechanism means comprises a contractible linkage means for avoiding an extension from an outer wall of the housing.

22. A blood pump useful as a ventricle assist or replacement device comprising:

a housing having a blood chamber, a drive chamber and a means for blood ingress and egress to and from the chamber;

a deflectable diaphragm comprising a wall of the blood chamber;

a pusher plate in operative association with the diaphragm;

means for selectively driving the pusher plate;

a telescoping guide mechanism in operative association with a pusher plate and generally disposed in the drive chamber for reciprocal movement in concert with selective operation of the diaphragm.

23. The pump as defined in claim 22 wherein the guide mechanism is disposed within the housing.

24. The pump as defined in claim 23 wherein the guide mechanism includes a nestable sleeve in operative engagement with the pusher plate.

25. The pump as defined in claim 22 wherein the housing includes an inner housing and an outer housing, the diaphragm generally disposed intermediate the inner and outer housing to define the blood chamber and the drive chamber.

26. The pump as defined in claim 22 wherein the guide mechanism includes a base having an outer wall contiguous to an outer wall of the housing and generally providing a smooth outer wall for the outer housing to avoid a significant guide mechanism projection from the housing.

27. A blood pump useful as a ventricle assist or replacement device comprising:

a housing having a blood chamber and a means for blood ingress and egress to and from the chamber;

a deflectable diaphragm comprising a wall of the blood chamber;

a pusher plate in operative association with the diaphragm;

means for selectively driving the pusher plate;

means for sensing a travel stroke of the pusher plate; and, a telescoping guide mechanism in operative association with a pusher plate.

28. The pump as defined in claim 27 wherein the sensing means comprises a Hall sensor and magnet assembly.

29. An implantable ventricular assist or replacement device particularly useful as a blood pump comprising:

a housing having a blood chamber, means for blood ingress and egress to and from the blood chamber, a drive chamber, and a segregating elastomeric diaphragm;

means for selectively pressurizing the drive chamber to pump blood to and from the blood chamber; and, the diaphragm including a pusher plate bonded thereto and having a plate guide mechanism comprising a plurality of nestable sleeves arranged for telescopic reciprocatory movement between extended and nested positions, the plurality of sleeves being disposed in the drive chamber in both the extended and nested positions to avoid a projection from the housing, said plurality of sleeves having means for limiting preselected maximum travel stroke to restrict enlargement of the drive chamber.

30. An implantable ventricular assist or replacement device particularly useful as a blood pump comprising:

a housing having a blood chamber, means for blood ingress and egress to and from the blood chamber, a drive chamber, and a segregating elastomeric diaphragm;

means for selectively pressurizing the drive chamber to pump blood to and from the blood chamber;

the diaphragm including a pusher plate bonded thereto and having a plate guide mechanism comprising a plurality of nestable sleeves arranged for telescopic reciprocatory movement between extended and nested positions, said plurality of sleeves having a means for limiting a preselected maximum travel stroke to restrict enlargement of the drive chamber; and, means for sensing a travel stroke of the pusher plate.

* * * * *